United States Patent
Colman et al.

(10) Patent No.: US 8,414,488 B2
(45) Date of Patent: Apr. 9, 2013

(54) MEDICAL SYSTEM, APPARATUS AND METHOD

(75) Inventors: Joshua Lewis Colman, Jerusalem (IL); David Lain, Easton, MD (US); John E. Auer, Ipswich, MA (US)

(73) Assignee: Oridion Medical 1987 Ltd., Har-Hotzvim (IL)

( * ) Notice: Subject to any disclaimer, the term of this patent is extended or adjusted under 35 U.S.C. 154(b) by 0 days.

(21) Appl. No.: 12/742,858

(22) PCT Filed: Nov. 13, 2007

(86) PCT No.: PCT/IL2007/001393
§ 371 (c)(1),
(2), (4) Date: Aug. 23, 2010

(87) PCT Pub. No.: WO2009/063443
PCT Pub. Date: May 22, 2009

(65) Prior Publication Data
US 2010/0317933 A1      Dec. 16, 2010

(51) Int. Cl.
*A61B 5/00* (2006.01)

(52) U.S. Cl.
USPC ........... 600/301; 600/323; 600/364; 600/481; 600/484; 600/529; 128/200.24; 128/920

(58) Field of Classification Search .......... 128/920–925; 600/300–301, 363–365, 372–374, 377–379, 600/382–384, 386–394, 481, 485, 500–503, 600/508, 515–519, 529–531, 544–547, 549, 600/587–595

See application file for complete search history.

(56) References Cited

U.S. PATENT DOCUMENTS

| | | | |
|---|---|---|---|
| 6,015,388 A * | 1/2000 | Sackner et al. | 600/529 |
| 6,188,407 B1 * | 2/2001 | Smith et al. | 715/841 |
| 6,402,697 B1 * | 6/2002 | Calkins et al. | 600/532 |
| 6,533,724 B2 * | 3/2003 | McNair | 600/300 |
| 6,796,305 B1 * | 9/2004 | Banner et al. | 128/204.21 |
| 7,031,857 B2 | 4/2006 | Tarassenko | |
| 2002/0120207 A1 * | 8/2002 | Hoffman | 600/538 |
| 2003/0106553 A1 | 6/2003 | Vanderveen | |
| 2003/0145854 A1 * | 8/2003 | Hickle | 128/204.18 |
| 2004/0236240 A1 | 11/2004 | Kraus | |
| 2004/0249249 A1 | 12/2004 | Lawson | |
| 2005/0177096 A1 * | 8/2005 | Bollish et al. | 604/65 |
| 2006/0195149 A1 * | 8/2006 | Hopper et al. | 607/11 |
| 2007/0010756 A1 * | 1/2007 | Viertio-Oja | 600/544 |
| 2007/0129647 A1 * | 6/2007 | Lynn | 600/538 |
| 2007/0167694 A1 * | 7/2007 | Causevic et al. | 600/301 |

(Continued)

OTHER PUBLICATIONS

Ailani, R. K et al "Dyspnea Differentiation Index* A New Method for the Rapid Separation of Cardiac vs Pulmonary Dyspnea", Chest, 116 (4) Oct. 1999, p. 1100-1104.*

(Continued)

*Primary Examiner* — Bill Thomson
*Assistant Examiner* — Marie Archer
(74) *Attorney, Agent, or Firm* — Rodney J. Fuller; Booth Udall Fuller, PLC (57) ABSTRACT

According to some embodiments, there is provided a medical monitoring device that includes one or more sensors, wherein a sensor is adapted to sense a parameter of a patient and computator adapted to receive an output of at least one sensor and to compute a condition-index-value directly related to a condition of the patient.

29 Claims, 4 Drawing Sheets

U.S. PATENT DOCUMENTS

| | | | |
|---|---|---|---|
| 2007/0179347 A1 | 8/2007 | Tarassenko | |
| 2008/0103378 A1* | 5/2008 | Kimball | 600/363 |
| 2008/0188733 A1* | 8/2008 | Al-Ali et al. | 600/364 |
| 2008/0230060 A1* | 9/2008 | Tham | 128/204.21 |
| 2008/0281168 A1* | 11/2008 | Gibson et al. | 600/301 |
| 2008/0300471 A1* | 12/2008 | Al-Ali et al. | 600/301 |
| 2009/0131805 A1* | 5/2009 | O'Brien et al. | 600/485 |
| 2009/0131810 A1* | 5/2009 | Oren et al. | 600/532 |
| 2009/0143694 A1* | 6/2009 | Krauss et al. | 600/532 |
| 2011/0040713 A1 | 2/2011 | Colman | |
| 2011/0082357 A1* | 4/2011 | Hornick | 600/364 |
| 2011/0208539 A1* | 8/2011 | Lynn | 705/2 |

OTHER PUBLICATIONS

Magalang, U. J et al "Prediction of the Apnea-Hypopnea Index From Overnight Pulse Oximetry", Chest, 124 (5) Oct. 2003, p. 1694-1701.*

Romero, P.V. et al "Physiologically based indices of volumetric capnography inpatients receiving mechanical ventilation", Eur Respir J 1997; 10: 1309-1315.*

Jantzen, Jan, Tutorial on fuzzy logic http://fuzzy.iau.dtu.dk/download/logic.pdf (20 pages) (1998).

Krauss, Baruch and Hess D. R., "Capnography for procedural sedation and analgesia in the emergency department", Ann Emerg Med, 50(2):172-181 (2007).

Quinlan, J. R., "Improved Use of Continuous Attributes in C4.5", Journal of Artificial Intelligence Research, 4:77-90 (1996).

Tarassenko, L. et al., "Integrated monitoring and analysis for early warning of patient deterioration", Br J Anaesth, 97(1):64-68 BJA Advance Access published May 17, 2006.

Tran, Tung and Zomorodi, Ali, "A Touch of Gray", Vertices, 10(1):11-12 (1994).

"Fuzzy logic for just plain folks", chapters 1-3, that may be found at http://www.fuzzy-logic.com/Ch1.htm, http://www.fuzzy-logic.com/Ch2.htm, http://www.fuzzy-logic.com/Ch3.htm (9, 7 and 13 pages respectively).

ISR of PCT/IL2007/001393 mailed Jul. 24, 2008.

Written opinion of PCT/IL2008/000894 mailed May 13, 2010.

IPRP of PCT/IL2008/000894 mailed May 18, 2010.

* cited by examiner

MEDICAL SYSTEM, APPARATUS AND METHOD

BACKGROUND

Medical monitoring devices are routinely used in various medical settings to provide crucial data regarding a patient's medical condition. The monitoring devices may be divided into two main groups: monitoring devices that are used to monitor parameters that are a direct measure of one of the patient's physiological functions and monitor device that are used to monitor parameters that are an indirect measure of the status of a physiological function. For example, a parameter that is a direct measure for a physiological function is capnography that may be used to measure and provides values of the $CO_2$ concentration in the ventilated breath, which is a direct measure of the patients ventilation functioning. For example, a parameter that is an indirect measurement is blood pressure, which indirectly provides information regarding the functioning of the heart and the cardio vascular condition of the patient.

Capnography is a non-invasive monitoring method used to continuously measure $CO_2$ concentration in exhaled breath. The $CO_2$, which is a constant metabolism product of the cells, is exhaled out of the body and the concentration of the exhaled $CO_2$, also known as end tidal $CO_2$ ($EtCO_2$) is an approximate estimation of the arterial levels of $CO_2$. The measurements of the $CO_2$ concentration in a breath cycle are performed by a capnograph and the results are a numerical value displayed also in a graphical format in the shape of a waveform named a capnogram. The numerical value of the results may be presented in units of pressure (mm Hg) or percentile. The capnogram may depict $CO_2$ concentration against total expired volume, but the more common capnogram illustrates $CO_2$ concentration against time.

Analyzing the capnogram may yield valuable information about the patient's clinical status. Normal capnogram exhibits one or more typical waveforms, each one represents a single respiratory cycle and deviation from the normal waveform may hint as to the clinical situation of the patient. For example, an abnormally high basal line represents re-breathing of exhaled $CO_2$; a slow increase in $CO_2$ concentration may hint to uneven emptying of the lungs; rising in $CO_2$ concentration without reaching a plateau may hint to situations of asthma or other lower airway obstruction, very small changes in $CO_2$ concentration may indicate an apnea situation, and the like. In addition to displaying respiratory cycles, a trend display is also available in which many individual consecutive breath cycles are compressed together so that changes over time may be easily distinguished, providing yet an additional aid in assessing and monitoring the patient's ventilation and clinical profile.

Capnography is widely used today as an important tool for tracking patient's ventilation status in various health care settings, such as Emergency Room (ER), Operation Room (OR), Intensive Care Unit (ICU) and Emergency Medical Services (EMS). Among the clinical applications in which capnography may be used are Cardiovascular (for example in CPR, shock, pulmonary embolism), Respiratory (for example, verification of endotracheal tubing, mechanically ventilated patients, conditions such as Asthma, hyperventilation, hypoventilation, apnea; Sedation (for example during operation); Patient transport (both intra- and inter-hospital).

In addition to $CO_2$ concentration, various other parameters may be indicative (directly or indirectly) of the ventilation (respiratory) status of a patient. Such parameters may include, for example, saturation of oxygen in the blood cells and other organs, heart rate, respiration rate, breath flow rate, blood pressure, and the like. Combination of various parameters may yield an improved indication clinical condition of the patient in general and of the ventilatory status of the patient in particular.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments there is provided a medical monitoring device that includes one or more sensors, wherein a sensor is adapted to sense at least one parameter of a patient and computator adapted to receive an output of at least one sensor and to compute an index-value directly related to a condition of the patient.

According to further embodiments, the parameter of a patient may include a respiratory related parameter, pulmonary related parameter, cardiac related parameter or any combination thereof. The parameter of a patient may include respiration rate, $EtCO_2$, $SpO_2$, heart rate, or any combination thereof. The one or more sensors may include a capnograph, pulse oximeter, heart rate monitor, or any combination thereof.

According to some embodiments, the index value may be in the range of 1 to 10. An increase in the index value may be indicative of an improvement in a patient's condition. A decrease in the index value may be indicative of a deterioration of a patient's condition.

According to some embodiments, the device computator may be adapted to compute the index value according to an average of an output of at least one sensor. The computator may further be adapted to compute the index-value according to a medical significance of an output of at least one sensor, wherein the medical significance may be determined by correlating the output value of the sensor and the ordinary level of a medical condition.

According to further embodiments, the device may be further adapted to compute a trend of the index-value. The device may be further adapted to compute a reliability index of the index-value. The device may additionally be adapted compute a pause frequency parameter.

According to further embodiments, the device may further be adapted to provide medical recommendation. The medical recommendation may be determined according to the index value. The medical recommendation may be determined according to the index value and a parameter related to a $CO_2$ waveform.

According to further embodiments, the device may further include a user interface. The device may also include a graphic display of the index value. The device may also provide indication correlating to a condition of the patient. The condition may include hyperventilation, hypoventilation or both. The device may further display sub regions of the index value, wherein the sub regions correlate to a condition of the patient.

According to some embodiments, there is provided a method for computing an index-value directly related to a condition of the patient, the method includes: a medical monitoring device comprising one or more sensors, wherein a sensor is adapted to sense at least one parameter of a patient and a computator adapted to receive an output of at least one sensor and compute said index value.

According to some embodiments, the at least one parameter of a patient may include a respiratory related parameter, pulmonary related parameter, cardiac related parameter and or combination thereof. The parameter of a patient may include respiration rate, EtCO2, SpO2, heart rate, or any combination thereof. The one or more sensors may include a capnograph, pulse oximeter, heart rate monitor, or any combination thereof.

According to some embodiments, the index value may be in the range of 1 to 10. An increase in the index value may be indicative of an improvement in a patient's condition. A decrease in the index value may be indicative of a deterioration of a patient's condition.

According to some embodiments, the device computator may adapted to compute the index value according to an average of an output of at least one sensor. The computator may further be adapted to compute the index-value according to a medical significance of an output of at least one sensor, wherein the medical significance may be determined by correlating the output value of the sensor and the ordinary level of a medical condition.

According to further embodiments, the device of the method may be further adapted to compute a trend of the index-value. The device may be further adapted to compute a reliability index of the index-value. The device may additionally be adapted compute a pause frequency parameter.

According to further embodiments, the device of the method may further be adapted to provide medical recommendation. The medical recommendation may be determined according to the index value. The medical recommendation may be determined according to the index value and a parameter related to a $CO_2$ waveform.

According to further embodiments, the device of the method may further include a user interface. The device may also display of the index value. The device may also provide indication correlating to a condition of the patient. The condition may include hyperventilation, hypoventilation or both. The device may further display sub regions of the index value, wherein the sub regions correlate to a condition of the patient.

According to some embodiments, there is provided a medical system that includes a monitoring device comprising one or more sensors, wherein a sensor is adapted to sense at least one parameter of a patient, computator adapted to receive an output of at least one sensor and to compute an index-value directly related to a condition of the patient and a sampling unit adapted to sample breath from a patient.

According to some embodiments, the sampling unit of the medical system may include an oral nasal cannula.

According to some embodiments, the parameter of a patient may include a respiratory related parameter, pulmonary related parameter, cardiac related parameter or any combination thereof. The parameter of a patient may include respiration rate, EtCO2, SpO2, heart rate, or any combination thereof. The one or more sensors may include a capnograph, pulse oximeter, heart rate monitor, or any combination thereof.

According to some embodiments, the index value may be in the range of 1 to 10. An increase in the index value is indicative of an improvement in a patient's condition. A decrease in said index value is indicative of a deterioration of a patient's condition.

In addition to the exemplary aspects and embodiments described above, further aspects and embodiments will become apparent by reference to the figures and by study of the following detailed descriptions.

BRIEF DESCRIPTION OF THE FIGURES

FIG. 1B—A graph depicting the respiration rate medical significance level;

FIG. 1C—A graph depicting the $SpO_2$ medical significance level;

FIG. 1D—A graph depicting the heart rate medical significance level; and

DETAILED DESCRIPTION

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

As referred to herein the terms "user", "medical user" and "health care provider", "health care professional" may interchangeably be used. The terms may include nay health care provider that may treat and/or attend to a patient. A user may include, for example, a nurse, respiratory therapist, physician, anesthesiologist, and the like.

As referred to herein, the terms "device", "monitoring device" and "medical device" may interchangeably be used.

As referred to herein, the terms "patient", subject" may interchangeably be used and may relate to a subject being monitored by any monitoring device for any physical-condition related parameter and/or health related parameter.

As referred to herein, the terms ordinary, normal, typical, standard, common may interchangeably be used.

As referred to herein, the terms "condition-index-value" and "index value" may interchangeably be used.

Currently, in most health care settings, patient related parameters (data) are collected on line and may provide various health care providers, such as a nurse, a physician, a respiratory therapist, an anesthesiologist and the like, with information regarding the patient's status. The information routinely presented may include various types of information regarding various parameters that may be sensed by various sensors. Viewing and interpreting the information presented may sometimes be a cumbersome, complicated and time consuming task for the health care provider.

According to some embodiments, there is a need to analyze the various patient related parameters (data) that are collected on line, in real time, and provide the health care providers with a more comprehensible, meaningful, intuitive, clearer and useful information about the patient status. The data collected may be calculated and the information to the health care provider may be provided in the form of a condition-index-value that is directly related to the clinical condition of the patient. The condition-index-value may be calculated based upon various parameters of a patient that may be sensed/measured by appropriate sensors. Providing the condition-index value to the health care provider may result in a clear indication for the health care provider to realize when more medical attention is required for a given patient and for a given patient condition. Since the condition-index value and the indications resulting therefrom may be deduced from several parameters, the sensitivity of monitoring the patient condition may be increased, and earlier warnings with earlier intervention may be anticipated.

According to further embodiments, the condition-index-value may be calculated/computed by a device, such as, for example, a monitoring device. The monitoring device may include one or more sensors that may be used to sense and/or measure, and/or calculate various health related parameters. The monitoring device may include any known medical monitoring device, such as, for example, capnograph, oxymeter, spirometer, heart rate sensors, blood pressure sensors, ECG, EEG, Ultrasound, and the like, and any combination thereof. Based on the various measurements, the device may calculate the condition-index-value, and display the index alone or in combination with the various patient parameters that may be sensed/measured by appropriate sensors. In addition, the device may also provide medical recommendations to the user based on the analysis of the collected patient data. Moreover, the device may track and notify the health care provider regarding changes over time of the patient condition. For example, the device may notify the health care provider if the patient condition is stable, improving or deteriorating.

According to some embodiments, the condition-index-value may be a unit-less value in any predetermined range, such as, for example, in the range of 1 to 100. For example, condition-index-value may in the range of 1 to 10, wherein 10 indicates the best condition, and 1 indicates the worst condition. Within the range of 1 to 10, sub ranges (subdivisions) may be assigned. For example, a sub-range from 8 to 10 indicative of a stable, normal condition, where no intervention is needed. A sub-range of 6-7 may be indicative for the health care provider that more attention is needed patient re-evaluation is recommended. A sub range of below 5 may indicate to the health care provider that intervention is needed and patient re-evaluation may be necessary. In addition, the various sub-ranges of the condition-index-value may be assigned different graphical signs, when displayed to the health care provider. The different graphical signs may include, for example, different colors, different units, different letters, and the like. For example, for condition-index-value in the sub-range of 8 to 10, the value may be colored green, for condition-index-value in the sub-range of 5 to 7 the value may be colored yellow and for condition-index-value in the sub-range of below 5, value may be colored red. In addition, various other visual indicators may also be used to indicate changes that may be correlated with known physical conditions, such as for example, up and down arrows that may indicate, for example an increase or decrease, respectively, in one or more measured parameters.

According to some embodiments, the condition index value may be calculated by various means, such as, for example by use of mathematical equations, algorithms, formulas, and the like that may take into consideration one or more of the values or derivatives of the values of the parameters that are being measured by the monitoring device.

According to further embodiments, the change of the condition-index-value over time (referred to herein as condition-index-value trend) may be displayed graphically. The graphic display may exhibit the condition-index-value trended over the last "n" (time units) of monitoring. For example, n may be any time period in the range of 5 minutes to 12 hours. This display may be used to indicate the patient's status, such as, for example: stable, improving, deteriorating, as well as providing a depiction of the rate and change of the patient's status. Displaying of the condition-index-value trend may simplify the assessment of the changes in the condition of the patient as compared to assessing the patient condition based on the trend of the individual parameters When looking at the trends of the individual parameters, it may not be easy and intuitive to determine the patients status and change in status, without taking into consideration the absolute values of the individual parameters and their interactions.

According to further embodiments, the condition-index-value trend may be depicted as a graphic display of the condition-index-value over time. The duration period of the trend may be chosen to be over any time period in the range of, for example between 5 minutes to 12 hours of the last measurements. The resolution of the graphical display may change accordingly in correlation to the selected time period.

According to further embodiments, an index of reliability (referred to herein also as "reliability index" "RI") may also be determined. The index of reliability (referred to herein also as "reliability index" or "RI") may provide a measure of the reliability of the data and more specifically, the reliability of the condition-index-value. For example, the reliability index may be used to predict and anticipate artifacts. The reliability index may be determined, for example, by analysis of the $CO_2$ waveforms, as depicted by a capnogram. If breath flow is also measured, its waveforms may also be used for this purpose. The use of breath flow measurements may refine and improve the index of reliability. Breath flow waveforms strongly complement the waveforms created by the $CO_2$ measurement, since both measurements represent essentially the same event, which is the breath cycle. While the breath flow relates to the envelope of the waveform, the $CO_2$ relates to the $CO_2$ concentration within the envelope. Using both parameters may better reveal and uncover what is a measurement noise, artifact, and the like.

According to additional embodiments, a pause frequency parameter may be determined. This parameter may include a measure of events wherein no breathing is detected, over a period of time. The events of lack of breathing may include, for example pause and apnea events, and the pause frequency parameter may include a measure of patient's pause and apnea events over a period of time. The pause frequency parameter may be calculated from the $CO_2$ waveform, as obtained by the capnogram. A pause event may be defined, for example, as any inhalation stage that persists for longer than any number of seconds in the range of, for example, 5 to 40 seconds (such as for example 20 seconds), and proceeds after an exhalation period lasting less than any number of seconds in the range of, for example, 5 to 20 seconds (such as, for example, 10 seconds). The time periods may be determined, for example, according to the average time of the last three exhalation cycles. Such determination of a pause event may be used to exclude a slow, rhythmic breathing pattern from being defined as a group of pause events. In addition, a maximum time out of, for example, 100 seconds may be determined. If a pause is detected, a new pause can only be counted if at least three new, valid breath cycles were detected beforehand. Thus, the Pause Frequency Parameter may be defined by the number of pause events per period of time (such as for example, an hour). The pause frequency may be updated at any time intervals, such as for example, every 5 minutes, after the period of 1 hour. The values of the pause frequency may further be stored and used for the display of the pause frequency trend, wherein the trend data represent the change of the pause frequency over time. According to some exemplary embodiments, during the first hour (when insufficient data has accumulated), a value may be provided and updated, for example, every 15 minutes until 1 hour has been reached (wherein during this time period the frequency is calculated as if it was calculated for 1 hour). During this time period an indication showing that the pause frequency is still based on a shorter period than 1 hour may be displayed. Since the health care provider, such as a nurse, may not be constantly present next to the patient and/or the monitoring device, and may not constantly track (monitor) the patient condition, a parameter, such as the pause frequency parameter, which is a periodic type effect may not easily be observed by the health care provider if not otherwise tracked by the monitoring device. In addition, according to further embodiments, the pause amplitude parameter may also be determined. The pause amplitude parameter may be determined by measurements of the time length (such as, for example, in the range of 5 to 60 seconds) of each of the detected pause events and the dispersion of the time lengths of the pause events over a period of time (such as, for example, over a time period of 60 minutes).

According to some embodiments, the device may further include and display medical recommendations to the health care professionals. The medical recommendations may be deduced from analysis of at least some of the individual parameter values and patterns and comparison of the measured values and patterns to the known ranges and patterns of the individual parameters. These recommendations may be displayed in addition to the indications derived from the calculated condition-index-value.

According to some embodiments the medical device may include a user interface that may allow the user to select the data to be displayed and to control various operating parameters. Moreover, different displays may be included to accommodate different needs of the different users (such as a nurse, a physician, an anesthesiologist, and the like). Allowing the user to change the view of the data may permit the user to toggle through the different levels of information for further evaluation of a condition. For example, the basic screen may be display the condition-index-value and the condition-index-value trend data. Changing to the next display may reveal the actual (measured) data values and the trends of the values that relate to the parameters from which the condition-index-value is calculated. Further toggling the display may provide the pause frequency and other related analysis and calculation. The use of the various displays may also allow the user to focus on the parameters that caused an indication of an event and/or recommendation to the user.

According to further embodiments, the user interface may also allow the user to enter information that is characteristic for each patient. The use of characteristic patient information is necessary to allow accuracy of the various measurements and calculations. Such information may include, for example age, weight, height, sex, and the like, of the specific patient. In addition, classification detection means of various patients may be utilized, wherein the classification may be based on parameters such as, for example, age group, weight group, sex, and the like. Using such classification may allow the monitoring device to correct its settings to be appropriate for that relevant patient type and environment.

According to some exemplary embodiments, the condition-index-value may represent the respiratory status and/or the pulmonary status and/or the cardiac status of the patient. This may be accomplished by providing an index value that is calculated based upon various respiratory, pulmonary and cardiac parameters, such as, for example, but not limited to: $EtCO_2$, respiratory rate, breath flow rate, spirometry readings, $O_2$ saturation, $SpO_2$, blood pressure, blood gases, heart rate, Electrocardiogram (ECG), Electroencephalogram (EEG), Ultrasound measurements, such as heart echogram, and the like and any combination thereof.

As referred to herein, the term EtCO2 relates to End tidal CO2. The $CO_2$ is exhaled out of the body and the concentration of the exhaled $CO_2$, also known as end tidal $CO_2$ ($EtCO_2$) is an approximate estimation of the alveolar $CO_2$ pressure and thus of the arterial levels of $CO_2$. The measurements of the $CO_2$ concentration in a breath cycle are performed by a capnograph and the results are a numerical value displayed also in a graphical format in the shape of a waveform named a capnogram. The values of EtCO2 may be measured in units of pressure, such as, for example, mmHg.

As referred to herein, the term SpO2 relates to the saturation of peripheral oxygen. It is a measurement of the amount of oxygen attached to the hemoglobin in red blood cell in the circulatory system. SpO2 values are generally given as a percentage (for example, normal value is above 96%). SpO2 may be monitored and measured by various monitors, such as for example, Pulse Oximeter.

As referred to herein, the term Respiration Rate (RR) is defined as the number of breaths taken in a minute and it may change under various physiological and medical conditions. The rate may be abnormally high (tachypnea), abnormally low (bradypnea) or non-existent (apnea).

As referred to herein, the term Heart Rate (HR) relates to the number of heart pulses (beats) in a minute.

As referred to herein, the term "hypoventilation" relates to a state of respiratory depression that may occur when ventilation is inadequate to perform needed gas exchange. Hypoventilation may cause an increased concentration of carbon dioxide and respiratory acidosis. Hypoventilation may be caused by various medical conditions and/or by use of some drugs and medicines.

As referred to herein, the term "hyperventilation" relates to a state of breathing faster and/or deeper than necessary, thereby reducing the carbon dioxide concentration of the blood below normal.

According to some exemplary embodiments, the condition-index-value may be a Pulmonary/Respiratory Index value (also referred to herein as "PI") may be determined. The PI index may represent a measurement of the patient's respiratory status. It may be deduced from various measured parameters, such as, for example: $EtCO_2$, Respiration Rate, $SpO_2$ and Heart Rate. The PI may be indicative of the absolute patient condition. The PI may be a unit-less value in the range of 1 to 10, wherein 10 indicates the best condition, and 1 indicate the worst condition. Within the range of 1 to 10, sub ranges (subdivisions) may be assigned. For example, a sub-range from 8 to 10 indicative of a stable, normal condition, where no intervention is needed. A sub-range of 6-7 may be indicative for the health care provider that more attention is needed. A sub range of below 5 may indicate to the health care provider that intervention and/or patient re-evaluation and/or change in therapy is recommended. In addition, the various sub-ranges of the condition-index-value may be assigned different graphical signs, when displayed to the health care provider. The different graphical signs may include, for example, different colors, different units, different letters, and the like. For example, for condition-index-value in the sub-range of 8 to 10, the value may be colored green, for condition-index-value in the sub-range of 5 to 7 the value may be colored yellow and for condition-index-value in the sub-range of below 5, value may be colored red. In addition, various other visual indicators may also be used to indicate changes that may be correlated with known medical conditions, such as for example, up and down arrows that may indicate, for example a state of hyperventilation and hypoventilation, respectively.

According to some embodiments, the PI index value may be determined by various ways, using various calculation methods and various algorithms, as further detailed below herein. Generally, the PI may be deduced from various parameters and may be assigned the highest value, for example "10", when the individual values of the various parameters are well within their respective normal ranges. The PI value may decrease below "10" when the value of one or more of the individual parameters changes from the normal respective ranges for those parameters. The decrease of the PI value may be sharper when several individual parameters change together.

According to some embodiments, the PI value may be updated continuously and it may be calculated from an average of the values of the parameters that are used to produce the PI value. In addition, the averaging time used for the determination of the PI value may also be adaptive. For example, if there is an erratic measurement, the average time may increase. The erratic characteristics used for deciding the averaging time may result, for example, from the respiratory rate values, the $CO_2$ waveform, and any other suitable parameter that is used for the calculation of the PI.

According to further embodiments, the PI value may also be indicative of conditions such as hypoventilation and hyperventilation. When the PI is indicative of these conditions, an appropriate additional indicative signaling may be displayed, such as, for example an upward arrow (indicative of hyperventilation) and downward arrow (indicative of hypoventilation). The decision as to whether the patient's status is in either hypoventilation or hyperventilation may be based for example, upon the Respiratory Rate, when respiratory rate is one of the measured parameters.

According to some embodiments, there are various methods to calculate the PI value. Generally, various parameters may be measured and used for the calculation of the PI value. According to some exemplary embodiments, the PI may be calculated based on measuring the values of at least one of the parameters $EtCO_2$, Respiration Rate, $SpO_2$ and Heart Rate. The real time values of these parameters may be measured continuously. For example, an adaptive running average may be collected for all the 4 measured parameters (average $EtCO_2$, average respiratory rate, average heart rate and average $SpO_2$). This adaptive running average may be calculated by collecting the data displayed by the monitors that measure the parameters, each second, and averaging over a period of time (as explained below). In this way, the calculated average take into consideration not only the values collected over the last "x" number of seconds, but also the length of time the value was displayed. The PI may then be calculated using these average values. The averaging time period may be calculated and defined using an adaptive type algorithm. For example, the default time period may be in the range of 5 to 60 seconds, such as for example, 30 seconds. The time may increase in steps of, for example, 2 to 30 seconds, such as, for example, in steps of 15 seconds; and the maximum period of time may be in the range of 5 to 180 seconds, such as, for example, 90 seconds, 120 seconds, and the like. In order to evaluate if the data is stable or erratic, information that may be used to determine if averaging time is to be increased or decreased, respectively, the parameter value of respiratory rate may be used. The standard deviation of the respiratory rate over the last predetermined period of time (such as, for example, 30 seconds) may be continuously measured. If the standard deviation of the respiratory rate value is below a predefined threshold, then the averaging period does not change. If the standard deviation of the respiratory rate over the last predetermined period of time is above the predetermined threshold, then the averaging period may be increased (for example, by 15 seconds).

According to some embodiments, the PI may be calculated by using mathematic calculations. The calculation may be based on the measuring the values of at least one of the parameters $EtCO_2$, Respiration Rate (RR), $SpO_2$ and Heart Rate (HR) and the calculated average of those parameters, as detailed above herein. The calculations may relay on known defined ranges values for each of the measured parameters (in correlation with the patient characteristics, as detailed below). Meeting predefined conditions of the various measured parameters values result in an appropriate calculated PI value. For example, and as further detailed in Example 1, when the following conditions are realized the PI be 10 or 9 and no arrows, indicative of changes in condition are displayed: If RR is >12 & <28 and $EtCO_2$ is ≧28 & <44 and $SpO_2$ is >94%, Then: PI=10. If RR is >12 & <28 and $EtCO_2$ is ≧28 & <44 and $SpO_2$>90% & <94%, Then: PI=9.

Figure 1A:
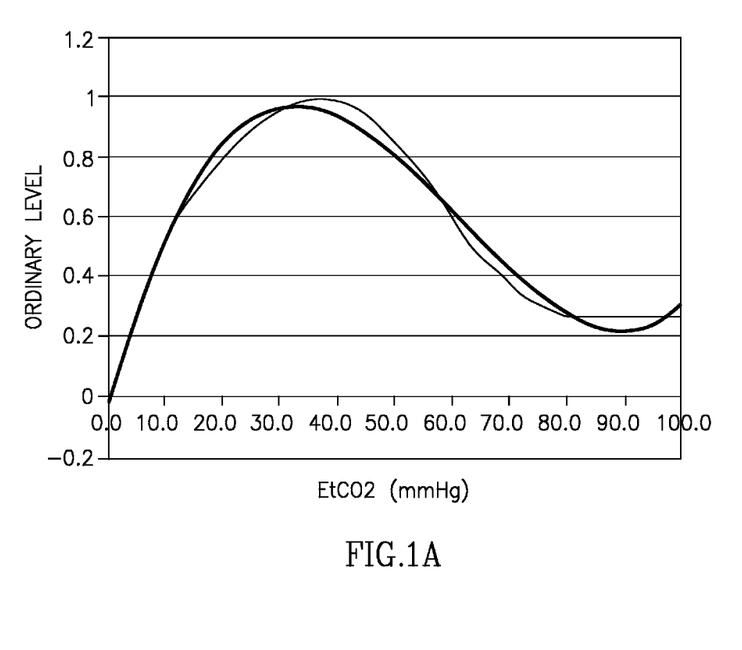
FIG. 1A—A graph depicting the $CO_2$ medical significance level.
Figure 1B:
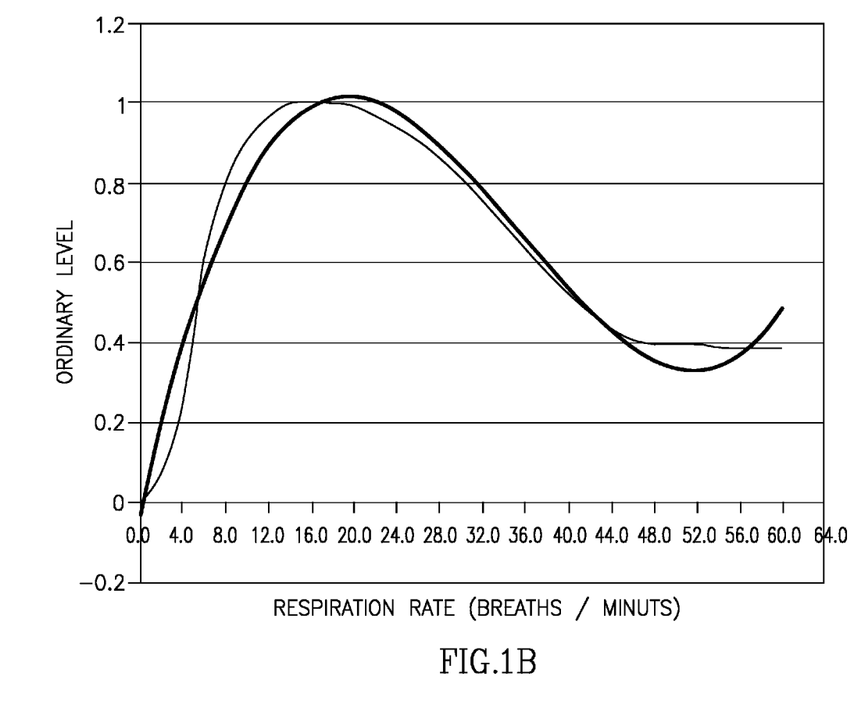
Figure 1C:
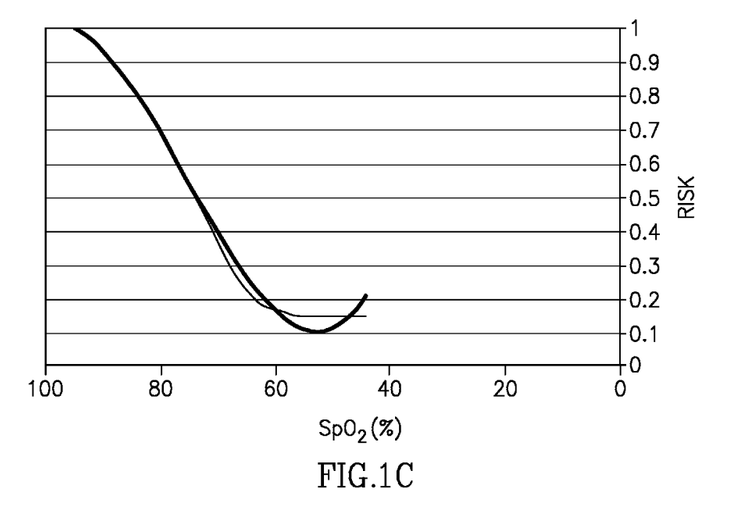
Figure 1D:
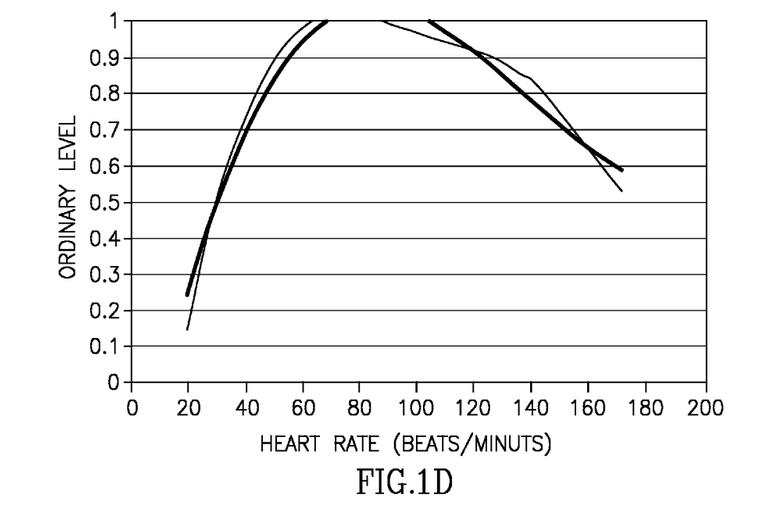

According to some embodiments, the PI may be calculated by using mathematic calculations. The calculations may be based on multiplication of the medical significance level (risk/probability level) that is associated with each of the measured parameters. The medical significance level of each of the measured parameters may be determined by creating a graph, indexing tables, and the like, which correlate the value of the parameter with an ordinary (standard/typical, common/normal) level of a physical condition, such as, for example ventilatory condition (such as breathing, respiration, exhaling, inhaling). The ordinary level of the physical condition may be in the range of 0 to 1, wherein 1 signifies the best physical condition and 0 signifies the worse physical condition. Thus, for example, mathematical functions may be provided for each of the measured parameters, where the maximum value of 1 may relate to a physical condition that is normal, and a minimum value of 0, may relate to a physical condition that is worst, such as for example, when no ventilatory performance is detected at all. FIG. 1A illustrates a graph which depicts the medical significance (risk levels) of the $EtCO_2$ parameter. As shown in FIG. 1A, the Y-axis is the ordinary level, in the scale of 0 to 1. The X-axis is the level of $EtCO_2$ in units of mmHg. The medical significance curve depicts the correlation curve between the ordinary level and the level of $EtCO_2$ and the calculated curve that best correlates to the medical significance curve. As can be deduced from the graph, at low $EtCO_2$ the ordinary level value decreases to zero, indicative of moving towards apnea, at high $EtCO_2$, although indicative of a dangerous condition (that may cause the blood to change its alkali level which may consequently many essential chemical processes), the ordinary level value does not fall to zero. The equation of the exemplary medical significance curve, which is illustrated in FIG. 1A may be described by the equation: $Y_1 = 8E-06 \times 3 - 0.0015 \times 2 + 0.0724 X[-] - 0.0496$. FIG. 1B illustrates an exemplary graph which depicts the medical significance levels of the respiration rate parameter. As shown in FIG. 1B, the Y-axis is the ordinary level, in a scale of 0 to 1. The X-axis is the respiratory rate in units of number of breaths in a minute. The medical significance curve depicts the correlation curve between the ordinary level and respiratory rate and the calculated curve that best correlates to the medical significance curve. The equation of the exemplary medical significance curve which is illustrated in FIG. 1B may be described by the equation: $Y_2 = 4E-05 \times 3 - 0.0043 \times 2 + 0.1231 X - 0.0378$. FIG. 1C illustrates an exemplary graph which depicts the medical significance levels of the $SpO_2$ parameter. As shown in FIG. 1C, the Y-axis is the ordinary level, in a scale of 0 to 1. The X-axis is the $SpO_2$ percentile. The medical significance curve depicts the correlation curve between the ordinary level and the $SpO_2$ and the calculated curve that best correlates to the medical significance curve. The exemplary equation of the medical significance curve which is illustrated in FIG. 1C may be described by the equation: $Y_3=-2E-05 \times 3+0.004 \times 2-0.2778X+6.1214$. FIG. 1D illustrates an exemplary graph which depicts the medical significance levels of the heart rate parameter. As shown in FIG. 1D, the Y-axis is the ordinary level, in a scale of 0 to 1. The X-axis is the heart rate that is measured in number of beats in a minute. The medical significance curve depicts the correlation curve between the ordinary level and the heart rate and the calculated curve that best correlates to the medical significance curve. The equation of the exemplary medical significance curve which is illustrated in FIG. 1D may be described by the equation: $Y_4=8E-07 \times 3-0.0003 \times 2+0.0406X-0.4389$. Similarly to creating and calculating the correlation equations, indexing tables may also be used to correlate between the ordinary level and the value of each of the measured parameters.

According to some embodiments, the PI may be calculated by multiplying the medical significance factors of each of the measured parameters, obtained by the equations detailed above herein, and multiplying the result by 10, to get an IP value in the range of 1 to 10. The equation may be described as: $PI=Y_1*Y_2*Y_3*Y_4$. According to some exemplary embodiments, the HR medical significance value ($Y_4$) is introduced to the calculations, only if the medical significance value of one of the other parameters is less than 0.8. In addition, the equations presented above herein are valid up to the following maximal values of the individual parameters: the $EtCO_2$ value reaches a value of about 90 mmHg, the respiratory rate reaches a value of about 50 bpm and $SpO_2$ reaches 50%. Above or below these values a default value of 0.2 may be used.

According to additional embodiments, if the calculated index is below 8, an upward arrow indication may be included if the respiration rate is greater than a predetermined number of beats per minute (BPM), such as, for example, 24 BPM. A downward arrow indication may be included if the respiration rate is below a predetermined number of BPM, such as, for example, 12 BPM. If the respiration rate is within a predetermined range, such as, for example between 12 and 24 BPM, no arrow indication is provided.

According to further embodiments, the change of the PI value over time (PI trend) may be displayed graphically. The graphic display may exhibit the PI trended over the last "n" (time units) of monitoring. For example, n may be any time period in the range of 5 minutes to 12 hours. This display may be used to indicate the patient's status, such as, for example: stable, improving, deteriorating, as well as providing a depiction of the rate and change of the patient's status. Displaying of the PI trend may simplify the assessment of the changes in the ventilatory condition of the patient as compared to assessing the patient condition based on the trend of the individual parameters When looking at the trends of the individual parameters, it may not be easy and intuitive to determine the patients status and change in status, without taking into consideration the absolute values of the individual parameters and their interactions, since both an increase or decrease in any of those parameters may be "good" (improvement) or "bad" (deterioration), depending on the absolute value of the parameter. For example, a decrease from a higher than normal absolute value towards the normal absolute value may be considered "good", while a decrease from a normal value to a lower than normal value may be considered "bad". Likewise, an increase from a lower than normal value towards the normal value may be considered "goof", while an increase from a normal value to a higher than normal value may be considered "bad". The PI trend may be depicted as a graphic display of the PI values over time. The duration period of the trend may be chosen to be over any time period in the range of, for example between 5 minutes to 12 hours of the last measurements. The resolution of the graphical display may change accordingly in correlation to the selected time period. By providing a trend of the PI index an estimation of how the patients respiratory status is changing over time, such as, stable, improving or deteriorating may be obtained. This may be attributed to the fact that the PI itself is an overall picture of the patients respiratory status and the changes in value of this index may provide a clear picture to whether the patient condition is changing or not.

According to further embodiments, an index of reliability may also be determined. The index of reliability (referred to herein also as "reliability index" or "RI") may provide a measure of the reliability of the data and more specifically, the reliability of the PI. For example, the reliability index may be used to predict and anticipate artifacts. The reliability index may be determined, for example, by analysis of the $CO_2$ waveforms, as depicted by a capnogram. If breath flow is also measured, its waveforms may also be used for this purpose. The use of breath flow measurements may refine and improve the index of reliability. Breath flow waveforms strongly complement the waveforms created by the $CO_2$ measurement, since both measurements represent essentially the same event which is the breath cycle. While the breath flow relates to the envelope of the waveform, the $CO_2$ relates to the $CO_2$ concentration within the envelope. Using both parameters may reveal and uncover and assist in distinguishing between a valid measurement, a noise, an artifact, and the like. The reliability index may assist the user (the health care provider) to decide if a low PI value or any of the other measured values is real (and represent a genuine clinical event), transient or an artifact. The reliability index may further assist the health care provider in assessing how much credibility may be attribute to the displayed PI value. In addition, the reliability index may allow the health care provider to detect artifacts, such as when the monitoring device is not placed properly on the patient, the monitoring device is not measuring properly, and the like. The reliability index may be determined from both analysis of the $CO_2$ waveform and respiration rate pattern. By obtaining data from controlled studies, the characteristic patterns attributed to artifacts may be defined. Analysis of the real time waveform depicted by the monitoring device and comparison to the known artifact patterns may be used to calculate the reliability index.

According to additional embodiments, a pause frequency parameter may be determined. This parameter may include a measure of events wherein no breathing is detected, over a period of time. The events of lack of breathing may include, for example pause and apnea events, and the pause frequency parameter may include a measurement of the patient's pause and apnea events over a period of time. Very often patients may stop breathing for short periods of time either because of mechanical obstructions or sometimes because a central (brain) block. The pauses (apnea events) are periodic and their frequency may be indicative of the condition of the patient. The pause frequency parameter may be calculated from the $CO_2$ waveform, as obtained by the capnogram. A pause event may be defined, for example, as any inhalation stage that persists for longer than any number of seconds in the range of, for example, 5 to 40 seconds (such as for example 20 seconds), and proceeds after an exhalation period lasting less than any number of seconds in the range of, for example, 5 to 20 seconds (such as, for example, 10 seconds). The time periods may be determined, for example, according to the average time of the last three exhalation cycles. Such determination of a pause event may be used to exclude a slow, rhythmic breathing pattern from being defined as a group of pause events. In addition, a maximum time out of, for example, 100 seconds may be determined. If a pause is detected, a new pause can only be counted if at least three new, valid breath cycles were detected beforehand. Thus, the pause frequency parameter may be defined by the number of pause events per period of time (such as for example, an hour). The pause frequency may be updated at any time intervals, such as for example, every 5 minutes, after the period of 1 hour. The values of the pause frequency may further be stored and used for the display of the pause frequency trend, wherein the trend data represent the change of the pause frequency over time. According to some exemplary embodiments, during the first hour (when insufficient data has accumulated), a value may be provided and updated, for example, every 15 minutes until 1 hour has been reached (wherein during this time period the frequency is calculated as if it was calculated for 1 hour). During this time period an indication showing that the pause frequency is still based on a shorter period than 1 hour may be displayed. Since the health care provider, such as a nurse, may not be constantly present next to the patient and/or the monitoring device, and may not constantly track (monitor) the patient condition, a parameter, such as the pause frequency parameter, which is a periodic type effect may not easily be observed by the health care provider if not otherwise tracked by the monitoring device. In addition, according to further embodiments, the pause amplitude parameter may also be determined. The pause amplitude parameter may include the time length (such as, for example, in the range of 5 to 60 seconds) of each of the detected pause events and the dispersion of the time length of those pause events over a period of time (such as, for example, over a time period of 60 minutes).

According to some embodiments, the monitoring device may further include and display medical recommendations to the health care professionals. The medical recommendations may be deduced from analysis of at least some of the individual parameters values and patterns and comparison of the measured values and patterns to the known ranges and patterns of the individual parameters. These recommendations may be displayed in addition to the indications derived from the calculated condition-index-value. The medical recommendations may be based on, for example, the characteristics of the $CO_2$ waveforms (presented as a capnogram) and RI values. The recommendation provided to the health care provider may include, for example such recommendation as: If $CO_2$ waveforms are observed with characteristics indicative of a partial obstruction (such as long downward slope of the waveform), then the device may recommend "open airway" or "check airway". If the $CO_2$ waveforms are very low but exhibit an excellent form indicative of low blood flow to lungs, then the device monitor may recommend: "check blood pressure" or similar. The detection of known $CO_2$ waveform patterns, which are indicative of known patient conditions that should and could be treated to improve the patient care, may be used in triggering and issuing the recommendations to the health care professional. For example, it is very common that a patient entering partial obstruction promote a waveform pattern wherein the downward slope of the capnogram increases in time, with a gradual fall. In such an instance, a notification to the health care provider, such as, "check patient airway" may be issued. For example, if the $CO_2$ waveforms pattern become very rounded and low, which is indicative of a mechanical problem with the cannula of the capnograph, a recommendation, such as, "check cannula interface" may be issued. Those and other similar medical recommendations issued by the monitoring device may be presented in addition to the indications derived from the PI. Examples of such analysis of waveform pattern may be found in publication: Krause B and Hess D. R (2007) "Capnography for procedural sedation and analgesia in the emergency department", Ann Emerg Med. 50(2), Pages 172-81, incorporated herein by reference. For example, lower airway obstruction may be seen by a capnogram showing a curved ascending phase and up-sloping alveolar plateau that indicate the presence of acute bronchospasm or obstructive lung disease; For example, distinguishing between bradypneic hypoventilation from hyperventilation may be performed according to the CO2 wave form: while in the bradypneic hypoventilation decreased respiratory rate, high amplitude and wide capnogram are detected, in hyperventilation an increase in respiratory rate, low amplitude and narrow capnogram are detected.

According to some embodiments the medical device may further include a user interface that may allow the user to select the data to be displayed and to control various operating parameters. Moreover, different displays may be included to accommodate different needs of the different users (such as a nurse, a physician, an anesthesiologist, and the like). Allowing the user to change the view of the data may permit the user to toggle through the different levels of information for further evaluation of a condition. For example, the basic screen may be display the condition-index-value and the condition-index-value trend data. Changing to the next display may reveal the actual (measured) data values and the trends of the values that relate to the parameters from which the condition-index-value is calculated. Further toggling the display may provide the pause frequency and other related analysis and calculation. The use of the various displays may also allow the user to focus on the parameters that caused an indication of an event and/or recommendation to the user.

According to further embodiments, the user interface may also allow the user to enter information that is characteristic for each patient. The use of characteristic patient information is necessary to allow accuracy of the various measurements and calculations. Such information may include, for example, age, weight, height, sex, and the like of the specific patient as well as other patient related information, such as, intubation (if the patient is intubated or not). For example, the patient size and age may change the PI calculations: for an adult a respiration rate of 12 BPM would be normal, but 36 BPM would be considered high, whereas for a child, respiration rate of 12 may be considered low, while 36 BPM may be considered normal. In addition, classification detection means of various patients may be utilized, wherein the classification may be based on parameters such as, for example, age group, weight group, sex, intubation, and the like. Using such classification may allow the monitoring device to correct its settings to be appropriate for that relevant patient type and environment. In addition, the user interface may allow automatic detection of the type of the patient according to the measuring interface being used. For example, a tubing interface used to measure $CO_2$ in breath may be different between an adult and a child and accordingly, the user interface may automatically adjust the patient settings to match the patient size group.

According to some embodiments there is thus provided a medical device that may be used to monitor patient's health condition, such as respiratory and/or pulmonary and/or cardiac status. The device may include, for example a canpongraphy device that may be adapted to sense and/or obtain measurements of various parameters other than $CO_2$. Such parameters may include, for example, $O_2$ levels, $O_2$ partial pressure, such as SpO2, heart rate, blood pressure, and the like. The device may further include a computator that may be used to receive information from at least one of the sensors and to compute a condition-index-value that is directly related to a condition of the patient. The condition index value may be in the range of 1 to 10, wherein 10 indicates the best condition while 1 indicates the worst condition. The monitoring device may further include one or display that may be used to present the data collected and calculated by the monitoring device. The display may present, for example, the calculated condition index in numerical format and in indexed format, wherein different ranges along the 1-10 scale of the calculated index may be assigned different colors; the change (trend) of the calculated condition index value over time; the reliability of the calculated index value; values and patterns of the various parameters measured by the various sensors of the monitoring device; graphical indications regarding the status of the patient, such as, for example, downward and upward arrows; and the like. The monitoring device may further be adapted to issue medical recommendations based upon the calculated condition index value and other measured parameters. In addition, the monitoring device may include a user interface that may allow the user to input patient related data that is specific for the patient, such as, for example, age, sex, size of the patient. The user interface may further allow the user to choose the parameters to be displayed and the form in which the parameters may be displayed, such as for example in the form of graphs, numerical values, indicators, and the like.

Figure 2:
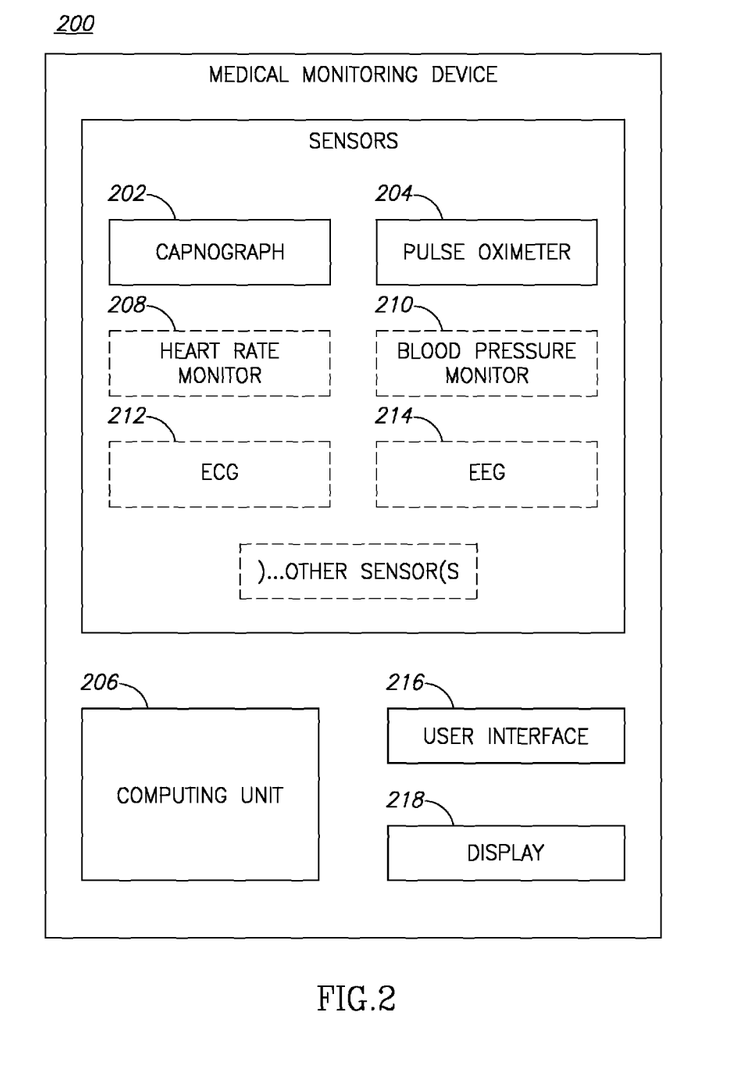
FIG. 2—A block diagram of a medical monitoring device, according to some embodiments.

Reference is now made to FIG. 2, which shows a block diagram of a medical monitoring device, according to some embodiments of the invention. Medical monitoring device 200 includes two sensors: capnograph 202 and pulse oximeter 204. Medical monitoring device 200 further includes computing unit 206 adapted to receive output parameters at least from capnograph 202 and from pulse oximeter 204. Computing unit 206 is further adapted to compute a unit-less index-value directly related to a respiratory status of the patient based on the output parameters. Medical monitoring device 200 may further include more sensors, such as heart rate monitor 208, blood pressure monitor 210, ECG 212 and EEG 214. Medical monitoring device 200 may further include user interface 216 and display 218.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

EXAMPLES

Example 1

Calculating PI Value Using Mathematical Methods

As detailed above herein, any of the parameter values used for the calculation of the PI is based on the calculated value of the average $EtCO_2$, average respiratory rate, average heart rate and average $SpO_2$.
$EtCO_2$—End tidal $CO_2$ is measured in units of mmHg
RR—Respiration Rate is measured in number of breaths per minute
$SpO_2$—is measured in percentile
HR—Heart Rate is measured in pulses per minute
PI≧9-10

When the following conditions are realized the index will be 10 or 9 and no arrows, indicative of hyper or hypoventilation, are displayed:

| | | |
|---|---|---|
| If RR is >12 & <28 | | |
| And EtCO2 ≧28 & <44 | | |
| And SpO2 >94% | Then: | Index = 10 |
| If RR is >12 & <28 | | |
| And EtCO2 ≧28 & <44 | | |
| And SpO2 >90% & <94% | Then: | Index = 9 |

PI≦7 and Indication of Hypoventilation

| | | |
|---|---|---|
| If RR is ≦5 | Then: | Index = 4 down |
| If RR is ≦8 | | |
| And EtCO2 ≧64 | | |
| Or EtCO2 ≦12 | | |
| Or SpO2 ≦86% | Then: | Index = 3 down |
| If RR is ≦5 | | |
| And EtCO2 ≧64 | | |
| Or EtCO2 ≦12 | | |
| And SpO2 ≦86% | Then: | Index = 1 down |
| If RR is ≦5 | | |
| And SpO2 ≦86% | Then: | Index = 2 down |
| If RR is >5 & ≦8 | | |
| And EtCO2 ≧46 & <64 | | |
| Or EtCO2 ≦24 & >12 | | |
| And SpO2 ≦90% & >86% | Then: | Index = 5 down |
| If RR is >5 & ≦8 | | |
| And EtCO2 ≧46 & <64 | | |
| Or EtCO2 ≦24 & >12 | | |
| And SpO2 >90% | Then: | Index = 6 down |
| If RR is >8 & ≦12 | | |
| And EtCO2 ≧55 | | |
| Or EtCO2 <18 | | |
| And SpO2 ≦90% | Then: | Index = 6 down |
| If RR is >8 & ≦12 | | |
| And EtCO2 ≧55 | | |
| Or EtCO2 <18 | | |
| And SpO2 >90% | Then: | Index = 7 down. |

PI≦8 and No Indication of Hyperventilation or Hypoventilation:

| | | |
|---|---|---|
| If RR is >12 & <16 | | |
| And $EtCO_2$ ≧ 64 | | |
| Or $EtCO_2$ < 12 | | |
| And SpO2 < 90% | Then: | Index = 6 |
| If RR is >12 & <16 | | |
| And $EtCO_2$ ≧ 64 | | |
| Or $EtCO_2$ < 12 | | |
| And $SpO_2$ > 90% | Then: | Index = 7 |
| If RR is >12 & <16 | | |
| And EtCO2 ≧44 & <64 | | |
| Or EtCO2 ≦24 & >12 | | |
| And SpO2 < 90% | Then: | Index = 7 |
| If RR is >12 & <16 | | |
| And EtCO2 ≧44 & <64 | | |
| Or EtCO2 ≦24 & >12 | | |
| And SpO2 > 90% | Then: | Index = 8 |

PI≦8 and Indication of Hyperventilation

| | | |
|---|---|---|
| If RR is ≧40 | | |
| And HR is ≧110 | Then: | Index = 4 Up |
| If RR is ≧40 | | |
| And EtCO2 ≧50 | | |
| And HR is ≧110 | Then: | Index = 3 Up |

-continued

| | | |
|---|---|---|
| If RR is ≧40 And EtCO2 ≧50 And HR is ≧110 And SpO2 ≦90% | Then: | Index = 2 Up |
| If RR is ≧40 And EtCO2 ≧44 & <50 And HR is ≧100 And SpO2 ≦90% | Then: | Index = 3 Up |
| If RR is ≧40 And EtCO2 ≧44 & <50 And HR is ≧100 And SpO2 >90% | Then: | Index = 4 Up |
| If RR is ≧32 & <40 And HR is ≧100 | Then: | Index = 8 Up |
| If RR is ≧32 & <40 And HR is ≧100 & <120 And EtCO2 ≧44 & <50 | Then: | Index = 7 Up |
| If RR is ≧32 & <40 And HR is ≧100 And EtCO2 ≧44 And SpO2 ≦90% | Then: | Index = 6 Up |
| If RR is ≧32 & <40 And HR is ≧120 And EtCO2 ≧55 | Then: | Index = 5 Up |
| If RR is ≧28 & <32 And HR is ≧120 And EtCO2 ≧55 | Then: | Index = 6 Up |
| If RR is ≧28 & <32 And HR is ≧100 And EtCO2 ≧44 And EtCO2 ≧44 & <64 Or EtCO2 ≦24 & >12 And SpO2 <90% | Then: | Index = 7 Up |
| If RR is >16 & <28 And EtCO2 ≧44 & <64 Or EtCO2 ≦24 & >12 And SpO2 <90% | Then: | Index = 7 up |

What we claim is:

1. A medical monitoring device comprising:
two or more sensors adapted to sense at least two parameters of a patient, wherein said two or more sensors comprise at least a capnograph and a pulse oximeter; and
a computing unit adapted to continuously receive at least two output parameters at least from said capnograph and said pulse oximeter and to continuously compute single unit-less index-values based on integration of said at least two output parameters,
wherein the single unit-less index-value is indicative of a respiratory status of the patient; such that a change in the single unit-less index-value is indicative of a change in the patient respiratory status.

2. The medical monitoring device of claim 1, wherein said at least two parameters of a patient comprises a respiratory related parameter, pulmonary related parameter, cardiac related parameter or any combination thereof.

3. The medical monitoring device of claim 1, wherein at least two parameters of a patient comprises respiration rate, EtCO2, $SpO_2$, heart rate, or any combination thereof.

4. The medical monitoring device of claim 1, wherein two or more sensors further comprise a heart rate monitor, blood pressure monitor, ECG, EEG, or any combination thereof.

5. The medical monitoring device of claim 1, wherein said single unit-less index-value is in the range of 1 to 10.

6. The medical monitoring device of claim 1, wherein an increase in said unit-less index-value is indicative of an improvement in a patient's status.

7. The medical monitoring device of claim 1, wherein a decrease in said unit-less index-value is indicative of a deterioration of a patient's status.

8. The medical monitoring device of claim 1, wherein said computing unit is adapted to compute said single unit-less index-value according to an average of an output of at least one sensor.

9. The medical monitoring device of claim 1, wherein said computing unit is adapted to compute said single unit-less index-value by mathematical operation of a medical significance level of each of the at least two output parameters.

10. The medical monitoring device of claim 9, wherein said medical significance level of each of the at least two output parameters is determined by correlating the output value of each of said at least two output parameters with that of a normal level.

11. The medical monitoring device of claim 9, wherein said mathematical operation comprises multiplication.

12. The medical monitoring device of claim 1, wherein said device is further adapted to compute a trend of said single unit-less index-value.

13. The medical monitoring device of claim 1, wherein said device is further adapted to compute a reliability index of said singe unit-less index-value.

14. The medical monitoring device of claim 1, further adapted to provide a pause frequency parameter.

15. The medical monitoring device of claim 1, wherein said device is further adapted to provide medical recommendation.

16. The medical monitoring device of claim 15, wherein said medical recommendation is determined according to said single unit-less index-value.

17. The medical monitoring device of claim 15, wherein said medical recommendation is determined according to said single unit-less index-value and a parameter related to a $CO_2$ waveform.

18. The medical monitoring device of claim 1, further comprising a user interface.

19. The medical monitoring device of claim 1, further comprising a graphic display of said single unit-less index-value.

20. The medical monitoring device of claim 19, further comprising a graphic display of a trend of said single unit-less index-value.

21. The medical monitoring device of claim 1, further adapted to provide indications correlating to a status of the patient.

22. The medical monitoring device of claim 21, wherein said status comprises hyperventilation, hypoventilation or both.

23. The medical monitoring device of claim 1, further adapted to graphically display a sub-range to which single unit-less index-value is assigned, wherein the sub-range correlates to a level of normality of the respiratory status and/or to whether medical intervention is required.

24. The medical monitoring device of claim 23, wherein said sub-range is displayed with a different graphical sign according to said level of normality of the respiratory status and/or to whether medical intervention is required.

25. The medical monitoring device of claim 1, wherein said unit-less index-value is in the range of 1 to 100.

26. The medical monitoring device of claim 1, wherein a decrease in said single unit-less index-value is indicative of an improvement in a patient's status.

27. The medical monitoring device of claim 1, wherein an increase in said single unit-less index-value is indicative of a deterioration of a patient's status.

28. The medical monitoring device of claim 1, wherein said computing unit is further adapted to correlate said output parameters to a set of predefined conditions.

29. The medical monitoring device of claim 1, wherein said change is further displayed as up and down arrows indicating hyperventilation and hypoventilation respectively.

* * * * *